(12) United States Patent
Spitali et al.

(10) Patent No.: US 9,309,280 B2
(45) Date of Patent: Apr. 12, 2016

(54) PROTEIN PURIFICATION

(75) Inventors: Mariangela Spitali, Slough (GB);
Jonathan Symmons, Slough (GB);
Richard Whitcombe, Slough (GB);
Mark Robert Pearce-Higgins, Slough (GB)

(73) Assignee: UCB PHARMA, S.A., Brussels (BE)

( * ) Notice: Subject to any disclaimer, the term of this patent is extended or adjusted under 35 U.S.C. 154(b) by 404 days.

(21) Appl. No.: 13/812,654

(22) PCT Filed: Jul. 26, 2011

(86) PCT No.: PCT/EP2011/062837
§ 371 (c)(1),
(2), (4) Date: Apr. 3, 2013

(87) PCT Pub. No.: WO2012/013682
PCT Pub. Date: Feb. 2, 2012

(65) Prior Publication Data
US 2013/0184439 A1 Jul. 18, 2013

(30) Foreign Application Priority Data
Jul. 27, 2010 (GB) .................................. 1012603.5

(51) Int. Cl.
*C07K 1/18* (2006.01)
*C07K 1/36* (2006.01)
*C07K 16/24* (2006.01)
*C07K 19/00* (2006.01)

(52) U.S. Cl.
CPC ... *C07K 1/18* (2013.01); *C07K 1/36* (2013.01); *C07K 16/241* (2013.01); *C07K 2317/14* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 2007/0060741 A1* | 3/2007 | Kelley et al. | 530/387.1 |
| 2010/0136025 A1* | 6/2010 | Hickman et al. | 424/158.1 |

FOREIGN PATENT DOCUMENTS

| | | | |
|---|---|---|---|
| WO | WO 8905157 A | * | 6/1989 |
| WO | WO 03/102132 | | 12/2003 |
| WO | WO 2004/035792 | | 4/2004 |
| WO | WO 2007/108955 | | 9/2007 |
| WO | WO 2007/117490 | | 10/2007 |
| WO | WO 2009135656 A1 | * | 11/2009 |

OTHER PUBLICATIONS

O'Donnell et al. "A high capacity strong cation exchane resin for the chromatographic purificaiton of monoclonal antibodies and other proteins" PREP, 2007, pp. 1-13.*
WHO Drug information, "dapirolizumab pegol", 2013, vol. 27, No. 4, 2013, pp. 399 & 411.*
AdisInsight, "Dapirolizumab pegol" retrieved from http://adisinsight.springer.com/drugs/800020347 pp. 1-4, Dec. 2, 2015.*
Humphreys, D. P. et al. "Engineering of *Escherichia coli* to improve the purification of periplasmic Fab' fragments: changing the pI of the chromosomally encoded PhoS/PstS protein" *Protein Expression & Purification*, 2004, pp. 109-118, vol. 37.
Written Opinion in International Application No. PCT/EP2011/062837, Mar. 7, 2012, pp. 1-6.
Humphreys, D.P., et al., "Therapeutic antibody production technologies: Molecules, applications, expression and purification," *Current Opinion in Drug Discovery & Development*, 2001, vol. 4, No. 2, pp. 172-185.
Palomares, L.A., et al., "Production of Recombinant Proteins, Challenges and Solutions," *Methods in Molecular Biology*, vol. 267, *Recombinant Gene Expression: Reviews and Protocols*, $2^{nd}$ ed., 2004, Humana Press Inc., Totowa, NJ, pp. 15-51.

* cited by examiner

*Primary Examiner* — Daniel E Kolker
*Assistant Examiner* — James Rogers
(74) *Attorney, Agent, or Firm* — Saliwanchik, Lloyd & Eisenschenk

(57) ABSTRACT

The present invention relates to a process for the purification of an antibody fragment from a periplasmic cell extract comprising a first cation exchange chromatography step and a second anion exchange chromatography step.

20 Claims, 6 Drawing Sheets

Chromatogram from capture step on Capto S™

Chromatogram from second chromatography step on Capto Q™

SDS-PAGE analysis of Capture load, Capture eluate and anion exchange flow-through

| Lane | Sample |
|---|---|
| 1 | SeeBlue Markers |
| 2 | Capto S load |
| 3 | Capto Q load |
| 4 | Capto Q flow through |

HCP Western Blot before and after anion exchange column

Fig. 5

SEQ ID NO: 1 shows the amino acid sequence of CDRH1 of CDP870.

Asp Tyr Gly Met Asn

SEQ ID NO: 2 shows the amino acid sequence of CDRH2 of CDP870

Trp Ile Asn Thr Tyr Ile Gly Glu Pro Ile Tyr Ala Asp Ser Val Lys Gly

SEQ ID NO: 3 shows the amino acid sequence of CDRH3 of CDP870.

Gly Tyr Arg Ser Tyr Ala Met Asp Tyr

SEQ ID NO: 4 shows the amino acid sequence of CDRL1 of CDP870.

Lys Ala Ser Gln Asn Val Gly Thr Asn Val Ala

SEQ ID NO: 5 shows the amino acid sequence of CDRL2 of CDP870.

Ser Ala Ser Phe Leu Tyr Ser

SEQ ID NO: 6 shows the amino acid sequence of CDRL3 of CDP870.

Gln Gln Tyr Asn Ile Tyr Pro Leu Thr

SEQ ID NO: 7 shows the amino acid sequence of the light chain variable region CDP870

Asp Ile Gln Met Thr Gln Ser Pro Ser Ser Leu Ser Ala Ser Val Gly Asp Arg
Val Thr Ile Thr Cys Lys Ala Ser Gln Asn Val Gly Thr Asn Val Ala Trp Tyr
Gln Gln Lys Pro Gly Lys Ala Pro Lys Ala Leu Ile Tyr Ser Ala Ser Phe Leu
Tyr Ser Gly Val Pro Tyr Arg Phe Ser Gly Ser Gly Ser Gly Thr Asp Phe Thr
Leu Thr Ile Ser Ser Leu Gln Pro Glu Asp Phe Ala Thr Tyr Tyr Cys Gln Gln
Tyr Asn Ile Tyr Pro Leu Thr Phe Gly Gln Gly Thr Lys Val Glu Ile Lys

Fig. 5 (cont.)

SEQ ID NO:8 shows the amino acid sequence of the heavy chain variable region CDP870.

Glu Val Gln Leu Val Glu Ser Gly Gly Gly Leu Val Gln Pro Gly Gly Ser Leu
Arg Leu Ser Cys Ala Ala Ser Gly Tyr Val Phe Thr Asp Tyr Gly Met Asn Trp
Val Arg Gln Ala Pro Gly Lys Gly Leu Glu Trp Met Gly Trp Ile Asn Thr Tyr
Ile Gly Glu Pro Ile Tyr Ala Asp Ser Val Lys Gly Arg Phe Thr Phe Ser Leu
Asp Thr Ser Lys Ser Thr Ala Tyr Leu Gln Met Asn Ser Leu Arg Ala Glu Asp
Thr Ala Val Tyr Tyr Cys Ala Arg Gly Tyr Arg Ser Tyr Ala Met Asp Tyr Trp
Gly Gln Gly Thr Leu Val Thr Val Ser Ser

SEQ ID NO: 9 shows the amino acid sequence of a grafted anti-TNFα Fab CDP870 light chain.

Asp Ile Gln Met Thr Gln Ser Pro Ser Ser Leu Ser Ala Ser Val Gly Asp Arg
Val Thr Ile Thr Cys Lys Ala Ser Gln Asn Val Gly Thr Asn Val Ala Trp Tyr
Gln Gln Lys Pro Gly Lys Ala Pro Lys Ala Leu Ile Tyr Ser Ala Ser Phe Leu
Tyr Ser Gly Val Pro Tyr Arg Phe Ser Gly Ser Gly Ser Gly Thr Asp Phe Thr
Leu Thr Ile Ser Ser Leu Gln Pro Glu Asp Phe Ala Thr Tyr Tyr Cys Gln Gln
Tyr Asn Ile Tyr Pro Leu Thr Phe Gly Gln Gly Thr Lys Val Glu Ile Lys Arg
Thr Val Ala Ala Pro Ser Val Phe Ile Phe Pro Pro Ser Asp Glu Gln Leu Lys
Ser Gly Thr Ala Ser Val Val Cys Leu Leu Asn Asn Phe Tyr Pro Arg Glu Ala
Lys Val Gln Trp Lys Val Asp Asn Ala Leu Gln Ser Gly Asn Ser Gln Glu Ser
Val Thr Glu Gln Asp Ser Lys Asp Ser Thr Tyr Ser Leu Ser Ser Thr Leu Thr
Leu Ser Lys Ala Asp Tyr Glu Lys His Lys Val Tyr Ala Cys Glu Val Thr His
Gln Gly Leu Ser Ser Pro Val Thr Lys Ser Phe Asn Arg Gly Glu Cys

SEQ ID NO: 10 shows the amino acid sequence of a grafted anti-TNFα Fab CDP870 heavy chain.
Glu Val Gln Leu Val Glu Ser Gly Gly Gly Leu Val Gln Pro Gly Gly Ser Leu Arg Leu Ser Cys Ala
Ala Ser Gly Tyr Val Phe Thr Asp Tyr Gly Met Asn Trp Val Arg Gln Ala Pro Gly Lys Gly Leu Glu
Trp Met Gly Trp Ile Asn Thr Tyr Ile Gly Glu Pro Ile Tyr Ala Asp Ser Val Lys Gly Arg Phe Thr Phe
Ser Leu Asp Thr Ser Lys Ser Thr Ala Tyr Leu Gln Met Asn Ser Leu Arg Ala Glu Asp Thr Ala Val
Tyr Tyr Cys Ala Arg Gly Tyr Arg Ser Tyr Ala Met Asp Tyr Trp Gly Gln Gly Thr Leu Val Thr Val
Ser Ser Ala Ser Thr Lys Gly Pro Ser Val Phe Pro Leu Ala Pro Ser Ser Lys Ser Thr Ser Gly Gly Thr
Ala Ala Leu Gly Cys Leu Val Lys Asp Tyr Phe Pro Glu Pro Val Thr Val Ser Trp Asn Ser Gly Ala
Leu Thr Ser Gly Val His Thr Phe Pro Ala Val Leu Gln Ser Ser Gly Leu Tyr Ser Leu Ser Ser Val Val
Thr Val Pro Ser Ser Ser Leu Gly Thr Gln Thr Tyr Ile Cys Asn Val Asn His Lys Pro Ser Asn Thr Lys
Val Asp Lys Lys Val Glu Pro Lys Ser Cys Asp Lys Thr His Thr Cys Ala Ala

PROTEIN PURIFICATION

CROSS-REFERENCE TO RELATED APPLICATION

This application is the U.S. national stage application of International Patent Application No. PCT/EP2011/062837, filed Jul. 26, 2011, the disclosure of which is hereby incorporated by reference in its entirety, including all figures, tables and amino acid or nucleic acid sequences.

The Sequence Listing for this application is labeled "SeqList.txt" which was created on Jan. 4, 2013 and is 8 KB. The entire contents of the sequence listing is incorporated herein by reference in its entirety.

FIELD OF THE INVENTION

The present invention is in the field of protein purification. More specifically, it relates to a process for the purification of antibody fragments.

BACKGROUND OF THE INVENTION

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors. The protein of interest must be isolated from the mixture of compounds fed to the cells and from the by-products of the cells themselves (feed stream) to purity sufficient for use as a human therapeutic. The standards set by health authorities for proteins intended for human administration regarding impurities from the feed stream are very high. Many purification methods for proteins known in the art contain steps requiring the application e.g. of low or high pH, high salt concentration or other extreme conditions that may irreversibly jeopardize the biological activity of the protein to be purified and are therefore not suitable. Thus, separation of the desired protein to sufficient purity poses a formidable challenge. Historically, protein purification schemes have been predicated on differences in the molecular properties of size, charge and solubility between the protein to be purified and undesired protein contaminants. Protocols based on these parameters include size exclusion chromatography, ion exchange chromatography, differential precipitation and the like.

Antibodies and antibody fragments are of increasing importance in a range of therapeutic areas. One of the most important methods of producing antibodies antibody fragments is by recombinant technology. Such techniques use a host cell to express the desired antibody, or antibody fragment, which is then separated from the production medium and purified.

Antibodies require glycosylation and are therefore generally expressed in eukaryotic expression systems employing eukaryotic cells, in particular mammalian cells such as CHO, PER.C6, NS0, BHK or Sp2/0 cells. In eukaryotic expression systems the protein of interest expressed such as an antibody is generally secreted into the cell culture medium. The medium can subsequently be separated easily from the protein secreting cells, e.g. by centrifugation or filtration.

Almost all current industrial antibody purification platforms use protein A (described e.g. in WO 98/23645). Protein A is a cell surface protein found in the cell wall of the bacteria staphylococcus aureus that binds to the Fc portion of mammalian immunoglobulin. Protein A has a high affinity to human $IgG_1$ and $IgG_2$ and a moderate affinity to human IgM, IgA and IgE antibodies. Consequently, protein A purification is not well suited for antibody fragments that lack the Fc portion.

A protein that does not require glycosylation is preferably expressed in prokaryotic expression systems employing prokaryotic cells such as gram-negative bacteria. Particularly, an antibody that does not require glycosylation, for example an antibody fragment such as a Fab, an Fab' or a scFv is preferably expressed in such systems. Prokaryotic expression systems and in particular Escherichia coli (E. coli) systems or other gram-negative bacteria allow the manufacturing of proteins that do not require glycosylation, such as for example antibody fragments, in an economically attractive way. Manufacturing of proteins in E. coli is beneficial in particular due to due to lower costs of goods and faster drug development processes (Humphreys, 2003; Humphreys, 2003). Prokaryotic and in particular E. coli protein expression systems are well known in the art (Swartz, 2001; Jana and Deb, 2005; Terpe, 2006). Prokaryotic cells do not actively secrete a heterologous protein of interest expressed in the cell. Gram-negative prokaryotic cells such as E. coli, however, can be engineered such that heterologous proteins expressed in the cell, such as antibody fragments, are exported into the periplasmic space where they can form disulfide bonds. Isolation of these heterologous proteins from the periplasmic space requires the disruption of the outer membrane of the prokaryotic cells which results in substantial release also of host cell proteins (HCPs). Methods for disrupting the outer membrane of a gram-negative prokaryotic cell and subsequent harvest of the cell culture fluid containing the heterologous are well known in the art. Manufacturing of antibody fragments in E. coli also results in the production of by-products such as truncated light chains, gluthathione adducts of light chains and light chain dimers (Battersby et al., 2001).

Cell culture fluid (feed stream) harvested from prokaryotic expression systems such as E. coli expression systems and in particular periplasmic cell extract from gram-negative bacteria differs substantially from cell culture fluid harvested from eukaryotic expression systems in the relative amount and composition of HCPs, bacterial DNA and endotoxin which need to be separated from the heterologous protein of interest that is expressed in the prokaryotic or eukaryotic expression system. Concentration of HCP as well as complexity and heterogeneity of HCP depend on the expression system or cell line and the cell culture conditions (Arunakumari, 2007). Purification of antibody fragments expressed in prokaryotic expression systems, in particular in gram-negative prokaryotic expression systems, faces therefore a different set of challenges and requires different approaches (Humphreys and Glover, 2001). Basic principles of purification of monoclonal antibody fragments are known in the art (Spitali, 2009). There are two medicinal products currently approved by the US Food and Drug Administration (FDA) and the European Medicines Agency (EMA) which comprise an antibody fragment as active ingredient which is produced in microbial cells: certolizumab pegol (Cimzia®) comprises a Fab binding specifically to TNFα and ranibizumab (Lucentis®) is a Fab fragment binding specifically to vascular endothelial growth factor (VEGF). Purification of ranibizumab from microbial feed stream is performed using a process with four chromatography steps (Walsh, 2007). The medicinal product abciximab (ReoPro®) comprises the Fab fragment of the chimeric human-murine monoclonal antibody 7E3 which binds to the glycoprotein (GP) IIb/IIIa receptor of human platelets and inhibits platelet aggregation. The chimeric 7E3 antibody is produced by continuous perfusion in mammalian cell culture. The 48 Kd Fab fragment is obtained from the purified full length antibody after digestion with papain and column chromatography.

Affinity chromatography separates proteins on the basis of a reversible interaction between a protein (or group of proteins) of interest and a specific ligand coupled to a chromatography matrix. The interaction between the protein of interest and ligand coupled to the chromatography matrix can be a result of electrostatic or hydrophobic interactions, van der Weals' forces and/or hydrogen bonding. To elute the target molecule from the affinity medium the interaction can be reversed, either specifically using a competitive ligand, or non-specifically, by changing the pH, ionic strength or polarity. Affinity purification requires a biospecific ligand that can be covalently attached to a chromatography matrix. The coupled ligand must retain its specific binding affinity for the target molecules and, after washing away unbound material, the binding between the ligand and target molecule must be reversible to allow the target molecules to be removed in an active form. Despite its common use, affinity chromatography is costly, particularly at the industrial scale necessary to purify therapeutic proteins.

Ion exchange chromatography can be used to purify ionizable molecules. Ionized molecules are separated on the basis of the non-specific electrostatic interaction of their charged groups with oppositely charged molecules attached to the solid phase support matrix, thereby retarding those ionized molecules that interact more strongly with solid phase. The net charge of each type of ionized molecule, and its affinity for the matrix, varies according to the number of charged groups, the charge of each group, and the nature of the molecules competing for interaction with the charged solid phase matrix. These differences result in resolution of various molecule types by ion-exchange chromatography. Elution of molecules that are bound to the solid phase is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). Two general types of interaction are known: Anionic exchange chromatography mediated by negatively charged amino acid side chains (e.g. aspartic acid and glutamic acid) interacting with positively charged surfaces and cationic exchange chromatography mediated by positively charged amino acid residues (e.g. lysine and arginine) interacting with negatively charged surfaces. Anion exchangers can be classified as either weak or strong. The charge group on a weak anion exchanger is a weak base, which becomes de-protonated and, therefore, loses its charge at high pH. Diethylaminoethyl (DEAE)-cellulose is an example of a weak anion exchanger, where the amino group can be positively charged below pH~9 and gradually loses its charge at higher pH values. DEAE or diethyl-(2-hydroxy-propyl)aminoethyl (QAE) have chloride as counter ion, for instance.

An alternative to elution by increase in ion strength of the elution buffer (elution chromatography) is elution using of molecules which have a higher dynamic affinity for the stationary phase than the bound protein. This mode of performing ion-exchange chromatography is called displacement chromatography. Displacement chromatography is fundamentally different from any other modes of chromatography in that the solutes are not desorbed in the mobile phase modifier and separated by differences in migration rates (Tugcu, 2008). In displacement, molecules are forced to migrate down the chromatographic column by an advancing shock wave of a displacer molecule that has a higher affinity for the stationary phase than any component from the feed stream. It is this forced migration that results in higher product concentrations and purities compared to other modes of operation of high retention, followed by a constant infusion of a displacer solution into the column.

Dynamic binding capacity describes the amount of protein of interest which will bind to a chromatography resin in a column under defined flow conditions. The dynamic binding capacity for a chromatography resin is dependent on running conditions (e.g. flow rate, pH and conductivity), origin of the sample, sample preparation and the other binding impurities present. Dynamic binding capacities are determined by loading a sample containing a known concentration of the protein of interest, and monitoring the concentration in the column flow-through (Do et al., 2008). The dynamic binding capacity of an ion exchange resin is defined as the point during loading when the protein of interest starts to be recovered in the flow-through. Typically a value of 10% for the proportion of protein of interest in the flow-through compared to the load is used to define this point (McCue et al., 2003). For impurity removal, the threshold for the impurity in the flow-through is set according to criteria specific to the application.

WO 99/57134, WO 2004/024866 and WO 2007/117490 relate to processes for protein or antibody purification comprising ion exchange chromatography. The processes are exemplified using antibodies produced in mammalian cells. WO 2009/058812 relates to a process for antibody purification comprising cation exchange chromatography. The process is exemplified using antibodies produced in mammalian cells. WO 2007/108955 relates to a two-step non-affinity ion exchange chromatograph process for protein purification comprising cation exchange chromatography followed by ion exchange chromatography. The Example in WO 2007/108955 describes the purification of fully human antibody produced in mammalian cells. Multiple washing steps were performed during cation exchange chromatography and the eluate diluted prior to anion exchange chromatography. Humphreys et al. describes the purification of Fab' at a laboratory scale using cation exchange chromatography and ion exchange chromatography (Humphreys et al., 2004). WO 2004/035792 relates to the generation of E. coli strains expressing mutant PhoS protein in order to reduce PhoS protein impurities in antibody fragment preparations purified from bacterial cell culture.

CDP870 is a genetically engineered antibody fragment (Fab') chemically linked to a PEG moiety as described in WO 01/94585 (which is incorporated herein by reference in its entirety). CDP870 has potent human TNFα neutralizing properties.

There is a need in the art for methods of purifying antibody fragments from cell culture fluids harvested from prokaryotic and in particular gram-negative bacteria such as E. coli expression systems. There is particular need in the art for methods of purifying antibody fragments from periplasmic cell extracts harvested from prokaryotic and in particular gram-negative bacteria such as E. coli expression systems that are suitable to operate with cell extracts that contain a very high titer of antibody fragment or HCP or both antibody fragment and HCP. High titer expression of the antibody fragments require methods suitable for the purification of the large quantities of antibody fragments in an economical manner: reducing the column sizes, buffer usage and processing times (GE Healthcare data file 11-0025-76 AE, 2007).

SUMMARY OF THE INVENTION

Purification requirements and challenges differ substantially for proteins that have purified from bacterial cell culture from proteins that have to be purified from eukaryotic cell culture. Particular difficulties are faced when proteins need to be purified from periplasmic cell extracts of gram-negative bacteria due to e.g. the amount of bacterial host cell proteins present. Further difficulties have to be overcome when proteins needs be purified from gram-negative bacterial cultures that express heterologous proteins to a very high concentration.

The inventors have surprisingly found a new process for purification of an antibody fragment from a periplasmic cell extract wherein the process is highly efficient and suitable for periplasmic cell extract comprising antibody fragment at a high concentration.

In aspect the invention provides a process for the purification of an antibody fragment from a periplasmic cell extract comprising a first chromatography step to capture the antibody fragment wherein a mixture containing an antibody fragment is subjected to cation exchange chromatography and subsequently eluted to produce a first eluate containing the antibody fragment; and a second chromatography step wherein the first eluate is subjected to anion exchange chromatography to capture impurities and produce a flow through containing the antibody fragment, and recovering said antibody fragment.

In another aspect the invention provides a process for the purification of an antibody fragment from a periplasmic cell extract consisting essentially of a first chromatography step to capture the antibody fragment wherein a mixture containing an antibody fragment is subjected to cation exchange chromatography to subsequently eluted to produce a first eluate containing the antibody fragment; a first ultrafiltration is applied to the first eluate; a second chromatography step wherein the purified first eluate is subjected to anion exchange chromatography to capture impurities to produce a flow through containing the antibody fragment; and a second ultrafiltration applied to the flow through, and recovering said antibody fragment.

BRIEF DESCRIPTION OF THE FIGURES

FIG. 3 shows an SDS-PAGE analysis of capture load, capture eluate and anion exchange flow-through.

FIG. 5 shows the amino acid sequences of CDP870.

BRIEF DESCRIPTION OF THE SEQUENCES

Figure 1:
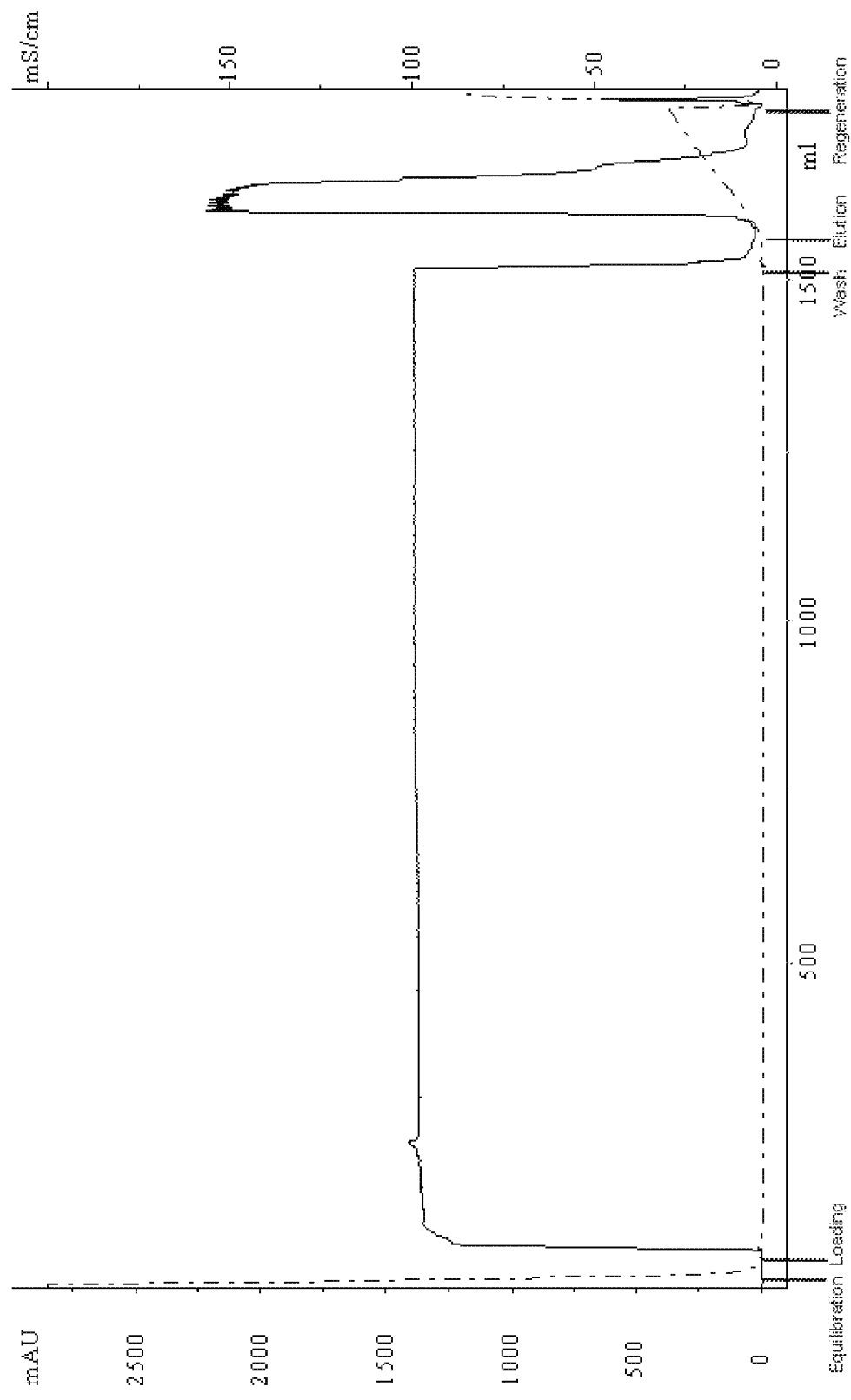
FIG. 1 shows a chromatogram of protein (including Fab') monitored by absorbance of UV light [measured in milli-absorbance units (mAU)] (solid line) along the conductivity (dotted line) from the first capture step on a cation exchange chromatography column (Capto S™). The chromatogram shows that a large volume can be loaded onto column during which some proteins do not bind, followed by the recovery of bound proteins including the Fab' in a small volume with an increase in conductivity.
Figure 2:
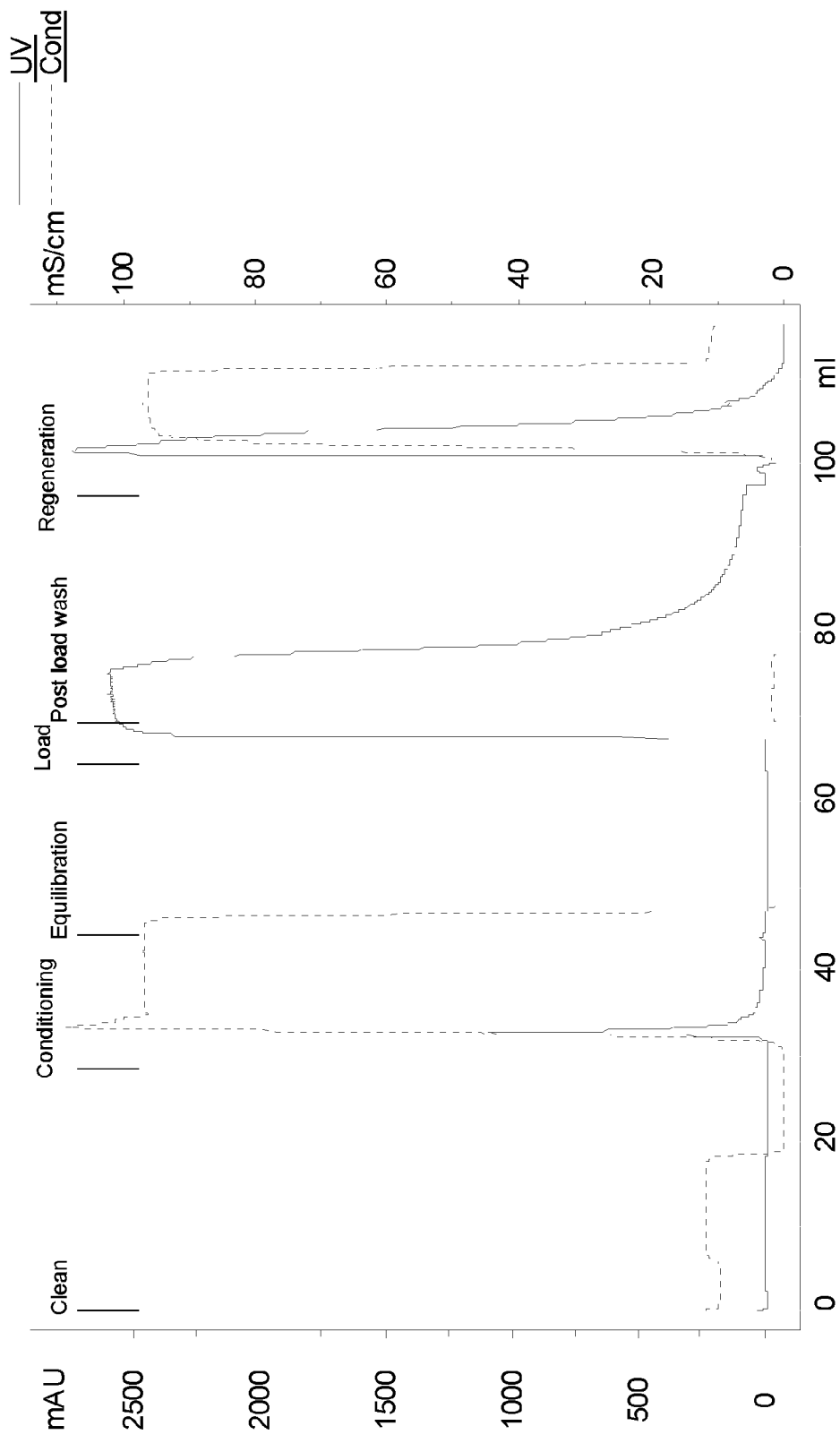
FIG. 2 shows a chromatogram from the step on an anion exchange chromatography column (Capto Q™). The chromatogram shows the non-binding of a Fab' and its appearance in the post-load wash with the bound impurities recovered in the regeneration peak.
Figure 3:
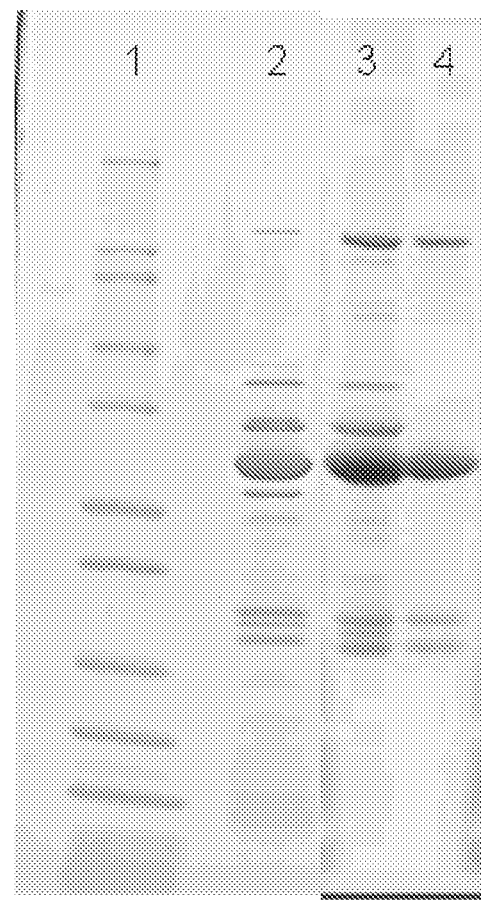
Figure 4:
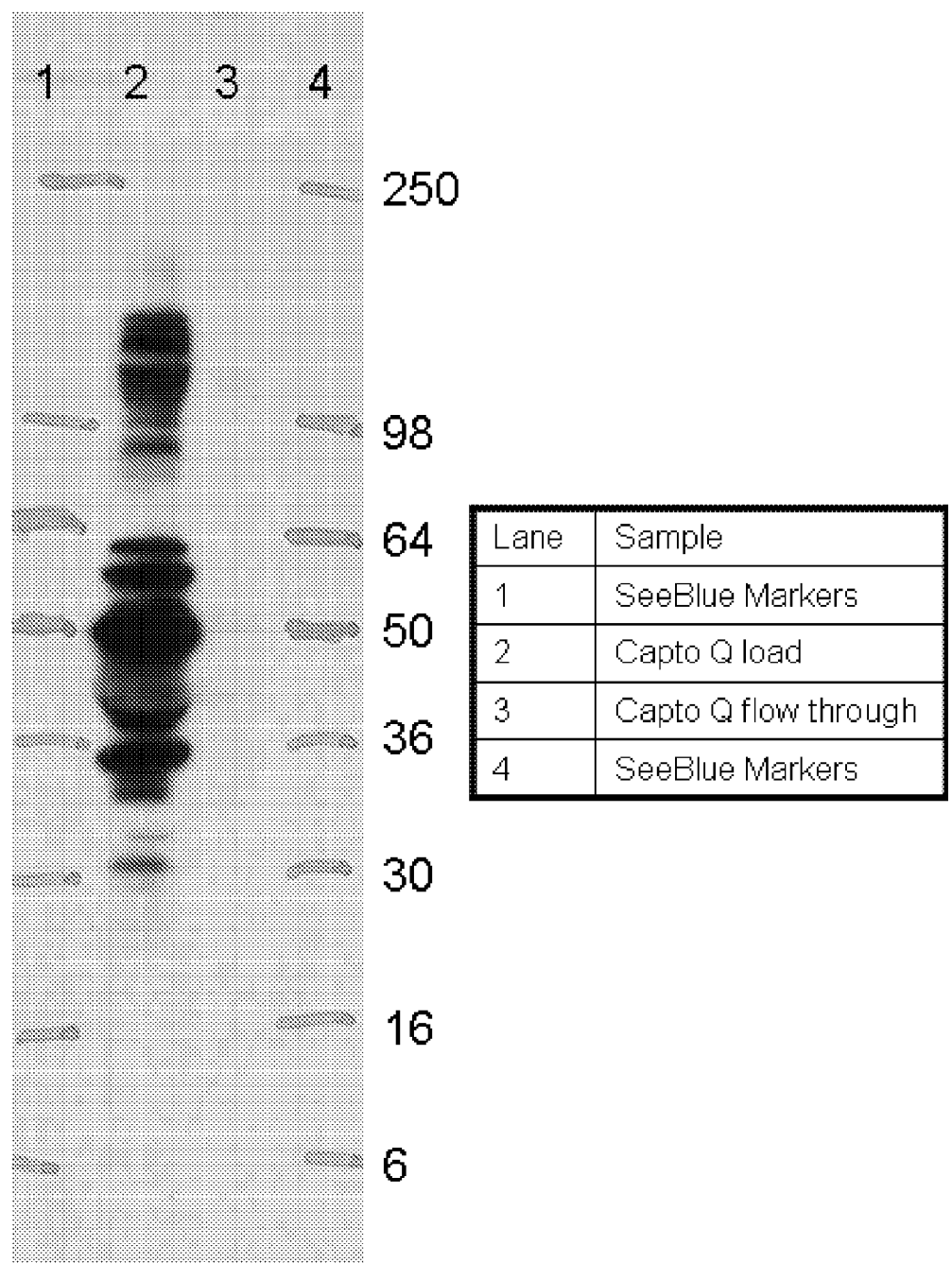
FIG. 4 shows Western-Blot to detect host cell proteins present in the sample before (Lane 2) and after (Lane 3) the anion exchange chromatography.

SEQ ID NO: 1 shows the amino acid sequence of CDRH1 of CDP870.

SEQ ID NO: 2 shows the amino acid sequence of CDRH2 of CDP870.

SEQ ID NO: 3 shows the amino acid sequence of CDRH3 of CDP870.

SEQ ID NO: 4 shows the amino acid sequence of CDRL1 of CDP870.

SEQ ID NO: 5 shows the amino acid sequence of CDRL2 of CDP870.

SEQ ID NO: 6 shows the amino acid sequence of CDRL3 of CDP870.

SEQ ID NO: 7 shows the nucleotide and predicted amino acid sequence of the light chain variable region CDP870.

SEQ ID NO: 8 shows the nucleotide and predicted amino acid sequence of the heavy chain variable region CDP870.

SEQ ID NO: 9 shows the amino acid sequence of a grafted anti-TNFα Fab CDP870 light chain.

SEQ ID NO: 10 shows the amino acid sequence of a grafted anti-TNFα Fab CDP870 heavy chain.

DETAILED DESCRIPTION OF THE INVENTION

In a first aspect the invention relates to a process for the purification of an antibody fragment from a periplasmic cell extract comprising a first chromatography step to capture the antibody fragment wherein a mixture, such as a periplasmic cell extract, containing an antibody fragment is subjected to cation exchange chromatography and subsequently eluted to produce a first eluate containing the antibody fragment; and a second chromatography step wherein the first eluate is subjected to anion exchange chromatography to capture impurities and produce a flow through containing the antibody fragment, and recovering said antibody fragment.

In a second aspect the invention relates to a process for the purification of an antibody fragment from a periplasmic cell extract consisting essentially of a first chromatography step to capture the antibody fragment wherein a mixture, such as a periplasmic cell extract containing an antibody fragment is subjected to cation exchange chromatography to subsequently eluted to produce a first eluate containing the antibody fragment; a first ultrafiltration applied to the first eluate; a second chromatography step wherein the purified first eluate is subjected to anion exchange chromatography to capture impurities to produce a flow through containing the antibody fragment; and a second ultrafiltration applied to the flow through, and recovering said antibody fragment.

In a first embodiment of the first aspect of the invention the process according to the first aspect of the invention comprises only two chromatography steps.

In a first embodiment of the second aspect of the invention the process according to the second aspect of the invention the ultrafiltration after the cation exchange chromatography and the ultrafiltration after the anion exchange chromatography are performed by tangential flow filtration (TFF).

In a second embodiment of the first or second aspect of the invention in the process according to the first embodiment of the first or second aspect of the invention all chromatography steps are performed on a chromatography column.

In a third embodiment of the first or second aspect of the invention in the process according to the first or second embodiment of the first or second aspect of the invention the cation exchange chromatography of the first chromatography step is performed in elution mode.

In a fourth embodiment of the first or second aspect of the invention in the process according to the second or third embodiment of the first or second aspect of the invention the cation exchange chromatography of the first chromatography step comprises the following steps in sequential order:

a) loading a mixture, such as a periplasmic cell extract, containing an antibody fragment onto the cation exchange column, b) washing the cation exchange column with a wash buffer wherein during the washing the conductivity, pH and salt concentration of the wash buffer is not changed, and c) eluting the antibody fragment with an elution buffer.

In a fifth embodiment of the first or second aspect of the invention in the process according to the fourth embodiment of the first or second aspect of the invention the pH of the washing buffer is identical to the pH of the mixture, such as a periplasmic cell extract, containing an antibody fragment, prior to the first chromatography step.

In a sixth embodiment of the first or second aspect of the invention in the process according to the first, second, third, fourth or fifth embodiment of the first or second aspect of the invention the mixture, such as a periplasmic cell extract, containing an antibody fragment, prior to the first chromatography step has a pH of between 4.0 to 5.0, preferably a pH of between 4.3 to 4.7, more preferably a pH of between 4.3 to 4.5 and most preferably 4.5.

In a seventh embodiment of the first or second aspect of the invention in the process according to the first, second, third, fourth, fifth or sixth embodiment of the first or second aspect of the invention the mixture containing an antibody fragment and being subjected to cation exchange chromatography as a primary capture step contains total protein at a concentration of at least 1.5 g/L, or at least 3 g/L, or at least 4 g/L, or at least 5 g/L, or at least 7.5 g/L, or at least 10 g/L or at least 20 g/L, or at least 40 g/L, or at a concentration of between 3 and 40 g/L, or at a concentration of between 4 and 20 g/L, or at a concentration of between 5 and 15 g/L.

In an eighth embodiment of the first or second aspect of the invention in the process according to the first, second, third, fourth, fifth, sixth or seventh embodiment of the first or second aspect of the invention the mixture containing an antibody fragment and being subjected to cation exchange chromatography as a primary capture step contains antibody fragment at a concentration of at least 3 g/L, or at least 4 g/L, or at least 5 g/L, or at least 7.5 g/L, or at least 10 g/L or at least 20 g/L, or at a concentration of between 3 and 20 g/L, or at a concentration of between 4 and 50 g/L, or at a concentration of between 5 and 10 g/L.

In a ninth embodiment of the first or second aspect of the invention in the process according to the first, second, third, fourth, fifth, sixth, seventh or eighth embodiment of the first or second aspect of the invention the cation exchange chromatography of the primary capture step is performed at a flow rate of at least 300 cm/h, preferably between 300 and 2000 cm/h, more preferably, between 350 and 1500 cm/h, even more preferably between 350 and 1000 cm/h, and most preferably between 400 and 700 cm/h.

In a tenth embodiment of the first or second aspect of the invention in the process according to the first, second, third, fourth, fifth, sixth, seventh, eighth or ninth embodiment of the first or second aspect of the invention the cation exchange chromatography of the primary capture step is performed at a conductivity of not more than 6 mS/cm, preferably between 6 and 2 mS/cm, more preferably between 5 and 3 mS/cm, and even more preferably between 4.5 and 3.5 mS/cm.

In an eleventh embodiment of the first or second aspect of the invention in the process according to the first, second, third, fourth, fifth, sixth, seventh, eighth, ninth or tenth embodiment of the first or second aspect of the invention the cation exchange chromatography of the primary capture step is performed on a resin comprising sulphonyl, sulphopropyl or carboxymethyl coupled to a resin of suitable material known in the art, including but not limited to crosslinked, beaded-forms of agarose (e.g. Sepharose™ or Superose™), modified methacrylate polymers (e.g. tentacle, hydroxylated); silica; ceramic and styrene divinylbenzene.

In a twelfth embodiment of the first or second aspect of the invention in the process according to the eleventh embodiment of the first or second aspect of the invention the resin of the cation exchange chromatography of the primary capture has a dynamic binding capacity for the antibody fragment of at least 50 g/L of resin, or at least 60 g/L of resin, or at least 75 g/L of resin, or at least 150 g/L resin, or between 50 and 150 g/L resin, or between 60 and 100 g/L resin, or between 50 and 75 g/L resin.

In an thirteenth embodiment of the first or second aspect of the invention in the process according to the eleventh or the twelfth embodiment of the first or second aspect of the invention the resin of the cation exchange chromatography of the primary capture has a mean particular size of at least 50 µm, preferably between 60 and 300 µm, more preferably between 70 and 200 µm, and even more preferably between 80 and 100 µm.

In a fourteenth embodiment of the first or second aspect of the invention in the process according to the first, second, third, fourth, fifth sixth, seventh, eighth, ninth, tenth, eleventh, twelfth or thirteenth embodiment of the first or second aspect of the invention the mixture containing an antibody fragment which is subjected to cation exchange chromatography in the primary capture step contains bacterial host cell protein in an amount of between about 200 µg/ml to 10,000 µg/ml, about 500 µg/ml to 5000 µg/ml, about 1000 µg/ml to 4000 µg/ml or about 2000 µg/ml to 4000 µg/ml.

In a fifteenth embodiment of the first or second aspect of the invention in the process according to the first, second, third, fourth, fifth, sixth, seventh, eighth, ninth, tenth, eleventh, twelfth, thirteenth or fourteenth embodiment of the first or second aspect of the invention the in the cation exchange chromatography of the primary capture step between 5 and 100 g antibody fragment per liter resin, between 10 and 90 g antibody fragment per liter resin or between 20 and 75 g antibody fragment per liter resin are loaded.

In a sixteenth embodiment of the first or second aspect of the invention in the process according to the first, second, third, fourth, fifth, sixth, seventh, eighth, ninth, tenth, eleventh, twelfth, thirteenth, fourteenth or fifteenth embodiment of the first or second aspect of the invention the anion exchange chromatography in the second chromatography step is performed on a resin comprising quaternary ammonium (Q), diethylaminoethyl (DEAE) or trimethylaminoethyl (TMAE) coupled to a resin of suitable material known in the art, including but not limited to crosslinked, beaded-forms of agarose (e.g. Sepharose™ or Superose™), modified methacrylate polymers (e.g. tentacle, hydroxylated); silica; ceramic and styrene divinylbenzene. The second chromatography step may also be performed on a membrane comprising a quaternary ammonium or poly(allylamine) coupled to a membrane of suitable material known to the art, including but not limited to cellulose and polyethylene.

In a seventeenth embodiment of the first or second aspect of the invention in the process according to the first, second, third, fourth, fifth, sixth, seventh, eighth, ninth, tenth, eleventh, twelfth, thirteenth, fourteenth, fifteenth or sixteenth embodiment of the first or second aspect of the invention the anion exchange chromatography column in the second chromatography step has a mean particular size of at least 50 µm, preferably between 60 and 300 µm, and more preferably between 70 and 200 µm, and even more preferably between 80 and 100 µm.

In a eighteenth embodiment of the first or second aspect of the invention in the process according to the first, second, third, fourth, fifth, sixth, seventh, eighth, ninth, tenth, eleventh, twelfth, thirteenth, fourteenth, fifteenth, sixteenth or seventeenth embodiment of the first or second aspect of the invention the anion exchange chromatography in the second chromatography step is performed at a pH of between 6 to 10, preferably a pH of between 7 to 9, more preferably between 8 to 9, and even more preferably at a pH of 8.5.

In an nineteenth embodiment of the first or second aspect of the invention in the process according to the first, second, third, fourth, fifth, sixth, seventh, eighth, ninth, tenth, eleventh, twelfth, thirteenth, fourteenth, fifteenth, sixteenth, seventeenth or eighteenth embodiment of the first or second aspect of the invention the anion exchange chromatography in the second chromatography step is performed has a binding capacity for the process-related impurities of greater than 20 g/L of resin, preferably greater than 30 g/L of resin, and even more preferably greater than 40 g/L of resin, or between 20 and 80 g/L resin, or between 20 and 40 g/L resin.

In a twentieth embodiment of the first or second aspect of the invention the process according to the first, second, third, fourth, fifth, sixth, seventh, eighth, ninth, tenth, eleventh, twelfth, thirteenth, fourteenth, fifteenth, sixteenth, seventeenth, eighteenth or nineteenth embodiment of the first or second aspect of the invention does not comprise a high performance tangential flow filtration (HPTFF) step.

In a twenty-first embodiment of the first or second aspect of the invention in the process according to the first, second, third, fourth, fifth, sixth, seventh, eighth, ninth, tenth, eleventh, twelfth, thirteenth, fourteenth, fifteenth, sixteenth, seventeenth, eighteenth, nineteenth or twentieth embodiment of the first or second aspect of the invention the antibody fragment recovered contains host cell protein (HCP) in an amount of not more than 150 parts per million (ppm), or not more than 120 ppm or not more than 100 ppm.

In further embodiments the process according to any of the embodiments of the first or second aspect of the invention wherein the antibody fragment is a Fab, Fab', F(ab')$_2$, Fv, a scFv or camelid antibody.

The term "affinity chromatography" as used herein, refers to a protein separation technique in which a protein of interest or antibody of interest is reversibly and specifically bound to a biospecific ligand. Preferably, the biospecific ligand is covalently attached to a chromatographic solid phase material and is accessible to the protein of interest in solution as the solution contacts the chromatographic solid phase material. The protein of interest (e.g. an antibody) retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the protein of interest to the immobilized ligand allows contaminating proteins or protein impurities to be passed through the chromatographic medium while the protein of interest remains specifically bound to the immobilized ligand on the solid phase material. The specifically bound protein of interest is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any substance can be used as a ligand for purifying its respective specific binding protein, e.g. antibody.

The terms "aglycosylated" and "non-glycosylated" are used interchangeably herein and refer to the lack of specific post-translational addition of a glycosyl- or carbohydrate moiety to a protein such as an antibody.

The term "antibody" or "antibodies" as used herein, refers to monoclonal or polyclonal tetrameric full length antibodies comprising two heavy and two lights chains.

The term immunoglobulin or immunoglobulins is used synonymously with "antibody" or "antibodies", respectively. The term "antibody" or "antibodies" as used herein includes but is not limited to recombinant antibodies that are generated by recombinant technologies as known in the art. An "antibody" or "antibodies" can be of any origin including from mammalian species such as human, non-human primate (e.g. human such as from chimpanzee, baboon, rhesus or cynomolgus monkey), rodent (e.g. from mouse, rat, rabbit or guinea pig), goat, bovine or horse species. The antibody herein is directed against an "antigen" of interest. Preferably, the antigen is a biologically important polypeptide and administration of the antibody to a mammal suffering from a disease or disorder can result in a therapeutic benefit in that mammal. However, antibodies directed against non-polypeptide antigens are also contemplated. Where the antigen is a polypeptide, it may be a transmembrane molecule (e.g. receptor) or ligand such as a growth factor or cytokine. Preferred molecular targets for antibodies encompassed by the present invention include CD polypeptides such as CD3, CD4, CD8, CD19, CD20, CD22, CD34, CD38, CD40 and CD40-L; FcRN; OX40; members of the HER receptor family such as the EGF receptor, HER2, HER3 or HER4 receptor; cell adhesion molecules such as LFA-1, Mac1, p150,95, VLA-4, ICAM-1, VCAM and av/b3 integrin including either α or β subunits thereof (e.g. anti-CD11a, anti-CD18 or anti-CD11b antibodies); chemokines and cytokines or their receptors such as IL-1α and β, IL-2, IL-6, the IL-6 receptor, IL-12, IL-13, IL-17 forms, IL-18, IL-21, IL-23, TNFα and TNFβ; growth factors such as VEGF; IgE; blood group antigens; flk2/flt3 receptor; obesity (OB) receptor; mpl receptor; CTLA-4; polypeptide C; etc.

The term "antibody fragment" or "antibody fragments" as used herein, refers an aglycosylated antibody or an aglycosylated portion of an antibody, generally the antigen binding or variable region thereof. Examples of antibody fragments include any antibody that lacks the or has no Fc portion. Examples of antibody fragments include also Fab, Fab', F(ab')$_2$, Fv and scFv fragments; diabodies; triabodies; tetrabodies; minibodies; antibodies consisting essentially of a single, two or three immunoglobulin domain(s) such as Domain Antibodies™; single-chain antibodies; bispecific, trispecific, tetraspecific or multispecific variants of any of the above. The term "antibody fragment" or "antibody fragments" as used herein also refers to camelid antibodies (e.g. from camels or llamas such as Nanobodies™) and derivatives thereof. Antibodies fragments are well known in the art (Holliger and Hudson, 2005). Various techniques have been developed for the production of antibody fragments and are known in the art (Glover and Humphreys, 2004). The term "antibody fragment" or "antibody fragments" as used herein, comprises human, humanized, primatized and chimeric antibody fragments.

The term "buffer" as used herein, refers to a substance which, by its presence in solution, increases the amount of acid or alkali that must be added to cause unit change in pH. A buffered solution resists changes in pH by the action of its acid-base conjugate components. Buffered solutions for use with biological reagents are generally capable of maintaining a constant concentration of hydrogen ions such that the pH of the solution is within a physiological range. Traditional buffer components include, but are not limited to, organic and inorganic salts, acids and bases.

The term "chromatography" as used herein, refers to the process by which a substance of interest in a mixture is separated from other substances in a mixture as a result of differences in rates at which the individual solutes of the mixture migrate through a stationary medium under the influence of a moving phase, or in bind and elute processes.

The term "chromatography column" or "column" in connection with chromatography as used herein, refers to a container, frequently in the form of a cylinder or a hollow pillar which is filled with the chromatography matrix or resin. The chromatography matrix or resin is the material which provides the physical and/or chemical properties that are employed for purification.

The term "conductivity" as used herein, refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSiemens per centimeter (mS/cm), and can be measured using a conductivity meter.

The conductivity of a solution may be altered by changing the concentration of ions therein. For example, the concentration of a buffering agent and/or concentration of a salt (e.g. NaCl or KCl) in the solution may be altered in order to achieve the desired conductivity.

The term "eluate" as used herein, refers to a liquid composition comprising the substance, (e.g. the antibody fragment or contaminant substance) which was obtained subsequent to the binding of said substance to a chromatography material and addition of an elution buffer to dissociate the substance from the chromatography material. Eluates may be referred to with respect to the step in the purification process. For example, the term "first eluate" refers to the eluate from the first chromatographic step; the term "second eluate" refers to the eluate from the second chromatographic step, etc.

The term "flow-through" as used herein, refers to a liquid composition comprising the substance, (e.g. the antibody fragment or contaminant substance) which was obtained by passing a mixture comprising said substance over a chromatography material such that the molecule passes over the material without binding.

The term "mixture", as used herein, refers to an at least partially liquid composition comprising at least one antibody fragment of interest which is sought to be purified from other substances which may also be present. Mixtures can, for example, be suspensions, aqueous solutions, organic solvent systems, or aqueous/organic solvent mixtures or solutions. The mixtures are often complex mixtures or solutions comprising many biological molecules (such as proteins, antibodies, hormones, and viruses), small molecules (such as salts, sugars, lipids, etc.) and even particulate matter. While a typical mixture of biological origin may begin as an aqueous solution or suspension, it may also contain organic solvents used in earlier separation steps such as solvent precipitations, extractions, and the like.

The term "periplasmic cell extract" as used herein, refers to the composition obtained from a cell culture of gram negative prokaryotic cells following the disruption of the outer membrane and release of material from the periplasmic space. A periplasmic cell extract is frequently liquid and may also contain particular matter or gas. The term "periplasmic cell extract" also includes a liquid composition that may have been treated further following the collection from the periplasmic space, e.g. to remove insoluble material.

The term "purification" or "purifying" or "purified" refers to a process wherein from a mixture containing a protein of interest, such as an antibody or antibody fragment, unwanted substances such as HCPs, DNA or salts are removed or reduced. A "purification step" may be part of an overall purification process resulting in a "homogeneous" composition, which is used herein to refer to a composition comprising less than 150 ppm HCP in a composition comprising the protein of interest, alternatively less than 120 ppm, less than 100 ppm, less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or less than 3 ppm.

The term "ultrafiltration" as used herein refers to a pressure-driven process wherein a mixture such as a solution, e.g. containing a protein of interest, is passed through a membrane for concentration or purification purposes. Ultrafiltration membranes typically have a mean pore size between 1 and 50 nm, which is between the mean pore size of reverse osmosis and microfiltration membranes. The pore size is usually quantified by its ability to retain proteins of certain molecular weights and is normally quoted in terms of a nominal molecular weight cut off (NMWCO) in kDa. Ultrafiltration separates solutes based on differences in the rate of filtration of different substances across the membrane in response to a given pressure driving force which rate is dependent on the size of the solute. Thus, the solutes in the mixture or solution are separated on the bases of size differences. Ultrafiltration is frequently used in downstream processing for protein concentration, buffer exchange and desalting, protein purification, virus clearance, and clarification. The term "ultrafiltration" includes tangential flow filtration (TFF) whereby the mixture such as solution is passed horizontally along the ultrafiltration membrane. The term "ultrafiltration" does not include high performance tangential flow filtration (HPTFF) whereby the solutes are separated not just on the basis of size, but size and charge.

The term "total protein" as used herein, refers essentially all proteins in a sample, including protein fragments of any size. Frequently, in connection with periplasmic cell extract or other cell culture harvest, "total protein" refers to both HCPs and heterologous protein expressed in the cell culture contained in a sample. Total protein can be determined using methods that are well known in the art.

An antibody fragment that can be purified in accordance with the methods of the present invention can be produced by culturing host cells transformed with one or more expression vectors encoding the recombinant antibody fragment. The host cells are preferably prokaryotic cells, preferably gram-negative bacteria. More preferably, the host cells are $E.\ coli$ cells. Prokaryotic host cells for protein expression are well known in the art (Terpe, 2006). The host cells are recombinant cells which have been genetically engineered to produce the protein of interest such as an antibody fragment. The recombinant $E.\ coli$ host cells may be derived from any suitable $E.\ coli$ strain including from MC4100, TG1, TG2, DHB4, DH5α, DH1, BL21, K12, XL1Blue and JM109. One example is $E.\ coli$ strain W3110 (ATCC 27,325) a commonly used host strain for recombinant protein fermentations. Antibody fragments can also be produced by culturing modified $E.\ coli$ strains, for example metabolic mutants or protease deficient $E.\ coli$ strains.

An antibody fragment that can be purified in accordance with the methods of the present invention is typically found in either the periplasm of the $E.\ coli$ host cell or in the host cell culture supernatant, depending on the nature of the protein, the scale of production and the *E. coli* strain used. The methods for targeting proteins to these compartments are well known in the art (Makrides, 1996). Examples of suitable signal sequences to direct proteins to the periplasm of *E. coli* include the *E. coli* PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, in the methods of the invention, the recombinant protein is expressed in the periplasm of the host *E. coli*.

Expression of the recombinant protein in the *E. coli* host cells may also be under the control of an inducible system, whereby the expression of the recombinant antibody in *E. coli* is under the control of an inducible promoter. Many inducible promoters suitable for use in *E. coli* are well known in the art and depending on the promoter; expression of the recombinant protein can be induced by varying factors such as temperature or the concentration of a particular substance in the growth medium. Examples of inducible promoters include the *E. coli* lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

*E. coli* host cell cultures (fermentations) may be cultured in any medium that will support the growth of *E. coli* and expression of the recombinant protein. The medium may be any chemically defined medium such as e.g. described in (Durany O, 2004).

Culturing of the *E. coli* host cells can take place in any suitable container such as a shake flask or a fermenter depending on the scale of production required. Various large scale fermenters are available with a capacity of more than 1,000 liters up to about 100,000 liters. Preferably, fermenters of 1,000 to 50,000 liters are used, more preferably 1,000 to 10,000 or 12,000 liters. Smaller scale fermenters may also be used with a capacity of between 0.5 and 1,000 liters.

Fermentation of *E. coli* may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the *E. coli* host cells and to allow higher cell densities to be reached.

If desired, the host cells may be subject to collection from the fermentation medium, e.g. host cells may be collected from the sample by centrifugation, filtration or by concentration. In particular, the methods of the invention are suitable for the large-scale industrial manufacture of antibodies of therapeutic quality.

In one embodiment the process according to the present invention comprises prior to the cation exchange chromatography capture step a step of centrifugation of cell culture harvest, followed by suspension of the host cells by addition of the extraction buffer.

For *E. coli* fermentation processes wherein the protein of interest such as an antibody fragment is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art.

In a preferred embodiment an extraction buffer is added to the sample and the sample is then subjected to a heat treatment step. The heat treatment step is preferably as described in detail in U.S. Pat. No. 5,655,866. The heat treatment step makes it possible to obtain a sample of soluble, correctly folded and assembled antibody fragment by facilitating the removal of other antibody-related material.

The heat treatment step is performed by subjecting the sample to a desired elevated temperature. Most preferably, heat treatment step is performed within the range of 30° C. to 70° C. The temperature can be selected as desired and may depend on the stability of the antibody for purification. In another embodiment, the temperature is within the range 40° C. to 65° C., or preferably within the range 40° C. to 60° C., more preferably within the range 45° C. to 60° C., even more preferably within the range 50° C. to 60° C. and most preferably at 55° C. to 60° C., 58° C. to 60° C. or 59° C. Thus, the minimum temperatures are 30° C., 35° C. or 40° C. and the maximum temperatures 60° C., 65° C. or 70° C.

The heat treatment step is preferably carried out for a prolonged period of time. The length of heat treatment is preferably between 1 and 24 hours, more preferably between 4 and 18 hours, even more preferably between 6 and 16 hours and most preferably between 10 and 14 hours or between 10 and 12 hours, for example 12 hours. Thus, the minimum time for heat treatment is 1, 2 or 3 hours and the maximum is 20, 22 or 24 hours.

In a particular embodiment, the heat treatment is performed at 50° C. to 60° C. for 10 to 16 hours, and more preferably at 59° C. for 10 to 12 hours. One skilled in the art will understand that temperatures and time can be selected as suits the sample in question and the characteristics of the antibody being produced.

Following the step of extraction the mixture containing the protein of interest such an antibody fragment may be subjected to a step of centrifugation and/or filtration prior to the step of adjusting the pH.

In further embodiments the process according to any of the embodiments of the first or second aspect of the invention is performed with an antibody fragment, for example a Fab or s Fab', that binds specifically to VEGF-A, glycoprotein IIb/IIIa receptor, C5, HER2/neu, TNFα, IL1β, CD40-L, OX40 or ICOS.

In a preferred embodiment of the invention the process according to any of the embodiments of the first or second aspect of the invention is performed with periplasmic cell extract comprising an antibody fragment which is an antibody fragment having specificity for human TNFα, more preferably CDP870, as described in WO 01/094585 (the contents of which are incorporated herein by reference).

In a one embodiment the antibody fragment having specificity for human TNFα, comprises a heavy chain wherein the variable domain comprises a CDR having the sequence shown in SEQ ID NO:1 for CDRH1, the sequence shown in SEQ ID NO:2 for CDRH2 or the sequence shown in SEQ ID NO:3 for CDRH3.

In one embodiment the antibody fragment comprises CDRs having the sequence shown in SEQ ID NO:4 for CDRL1, the sequence shown in SEQ ID NO:5 for CDRL2 or the sequence shown in SEQ ID NO:6 for CDRL3.

In one embodiment the antibody fragment comprises CDRs having the sequence shown in SEQ ID NO:1 for CDRH1, the sequence shown in SEQ ID NO:2 for CDRH2 or the sequence shown in SEQ ID NO:3 for CDRH3 and CDRs having the sequence shown in SEQ ID NO:4 for CDRL1, the sequence shown in SEQ ID NO:5 for CDRL2 or the sequence shown in SEQ ID NO:6 for CDRL3.

In one embodiment the antibody fragment comprises SEQ ID NO:1 for CDRH1, SEQ ID NO: 2 for CDRH2, SEQ ID NO:3 for CDRH3, SEQ ID NO:4 for CDRL1, SEQ ID NO:5 for CDRL2 and SEQ ID NO:6 for CDRL3.

The antibody fragment is preferably a CDR-grafted antibody fragment molecule and typically the variable domain comprises human acceptor framework regions and non-human donor CDRs.

Preferably, the antibody fragment comprises the light chain variable domain CDP870 (SEQ ID NO:7) and the heavy chain variable domain CDP870 (SEQ ID NO:8).

It is preferred that the antibody fragment is a modified Fab fragment wherein the modification is the addition to the C-terminal end of its heavy chain one or more amino acids to allow the attachment of an effector or reporter molecule. Preferably, the additional amino acids form a modified hinge region containing one or two cysteine residue to which the effector or reporter molecule may be attached. Such a modified Fab fragment preferably has a heavy chain comprising or consisting of the sequence given as SEQ ID NO:10 and the light chain comprising or consisting of the sequence given as SEQ ID NO:9.

In further embodiments the process according to any of the embodiments of the first or second aspect of the invention is performed with abciximab, ranibizumab, pexelizumab, CDP484, or CDP7657.

Equilibration

In further embodiments of the invention the cation exchange chromatography column for the primary capture step is equilibrated with an anionic buffer of suitable composition to buffer at the required pH and conductivity (for example 50 mM sodium acetate at pH 5 or 50 mM sodium lactate at pH 4.0. The equilibration can be achieved using at least 2 column volumes of the equilibration buffer, but may also include a two step equilibration process with two column volumes of a buffer containing 1 M NaCl (to ensure the column is adequately charged with the relevant counter cation) followed by at least 2 column volumes of the equilibration buffer.

In further embodiments of the invention the anion exchange chromatography column of the second chromatography step is equilibrated in the same way except that the equilibration buffer is ideally a cationic buffer e.g. 20 mM Tris HCl at pH 8.0 or 20 mM bis-Tris HCl at pH 7.0. The equilibration of the anion exchange chromatography column can also be achieved using a two step equilibration process with buffer containing 1 M NaCl (to ensure the column is adequately charged with the relevant counter anion) followed by the equilibration buffer; or a single step directly with the equilibration buffer.

Washing

In further embodiments of the invention after loading the cation exchange chromatography column for the primary step, it is washed with at least 2 column volumes of the equilibration buffer. Additional impurity may be removed by using a wash buffer with a higher conductivity, e.g. 0.5 mScm or higher conductivity.

In further embodiments of the invention after loading the anion exchange chromatography column for the second chromatography step, the column is washed with up to 2 column volumes of the equilibration buffer. Other buffers with similar pH and conductivity may also be used. Buffers with a higher conductivity are not recommended if the maximum removal of the process-related impurities is desired.

Elution

In further embodiments of the invention the antibody fragment is eluted from the cation exchange chromatography column in the primary capture step using a buffer either at a higher pH, a higher conductivity or a combination of the two. The increased conductivity can be achieved with the addition of NaCl (or other salt) to the equilibration buffer at a concentration of greater than 50 mM, preferably greater than 100 mM and even more preferably greater than 200 mM.

In further embodiments of the invention the elution of the antibody fragment from the anion exchange chromatography column in the second chromatography step occurs during the loading and wash steps. The bound process-related impurities can be eluted by using a buffer either at a lower pH, higher conductivity or a combination of both. Ideally, the higher conductivity should be at least 70 mS/cm.

Having now fully described this invention, it will be appreciated by those skilled in the art that the same can be performed within a wide range of equivalent parameters, concentrations and conditions without departing from the spirit and scope of the invention and without undue experimentation. While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth follows in the scope of the appended claims.

As used herein, "a" or "an" may mean one or more. The use of the term "or" herein is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein, "between X and Y" may mean a range including X and Y.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

EXAMPLES

Example 1

CDP870 Fab' was expressed as a heterologous protein in *E. coli* W3110 host cells at a concentration of 1.9 g/L. The heterologous protein was released from the periplasmic space of the host cells by the addition of Tris-EDTA and heat treatment at 50° C. Cellular material was removed through centrifugation and the cell extract containing the heterologous protein was adjusted through addition of acetic acid to a pH 4.5. The pH adjusted cell extract was then clarified using a combination of centrifugation and depth filtration with 0.2 µm filtration.

The clarified extract (feed stream) was diluted with a dilution factor of 4 with water to achieve a conductivity of 3.5 mS/cm.

The feed stream containing the CDP870 Fab' was then loaded to about 75 g/L resin at a flow rate of 400 cm/h onto a Capto S™ cation exchange column from GE Healthcare [highly cross-linked rigid agarose bead (mean particle size 90 µm) with a sulphonate cation exchange ligand attached via a dextran linker (ionic capacity 0.11-0.14 mmol $Na^+$/ml)]. The Capto S™ cation exchange column had a column bed height of 20 cm with a diameter of 7.7 mm. The column had been equilibrated prior to feed stream loading with 6 column volumes of 50 mM sodium acetate buffer adjusted to pH 4.5 with acetic acid.

After loading the column was washed with 5 column volumes of the 50 mM sodium acetate buffer adjusted to pH 4.5 with acetic acid, until the all the unbound material is washed off. The CDP870 Fab' fraction was eluted with a 20 column volumes gradient up to a concentration of 50 mM sodium acetate and 250 mM NaCl adjusted to pH 4.5 with acetic acid. The eluted CDP870 Fab' was collected when the UV absorbance at 280 nm exceeded 0.26 AU/cm until it dropped below 0.54 AU/cm.

The CDP870 Fab' pool was subjected to ultrafiltration in a centrifugal concentrator using a polyether sulphone-based ultrafiltration membrane with a nominal molecular weight cut-off of 10 kDa resulting in a concentration of the CDP870 Fab' pool to 6 mg/mL. Subsequently diafiltration was performed until the CDP870 Fab' pool in 20 mM Tris had reached pH 8.0 and a conductivity of 1.1 mS/cm. 6 volumes of buffer were required for the diafiltration.

The CDP870 Fab' pool was loaded onto a Capto™ anion exchange chromatography column from GE Healthcare [highly cross-linked rigid agarose bead (mean particle size 90 µm) with a quaternary amine anion exchange ligand attached via a dextran linker (ionic capacity 0.16-0.22 mmol $Cl^-$/ml)] at a flow rate of 500 cm/h and applying about 5 g of CDP870 Fab' per liter of resin. The Capto Q™ anion exchange column had a column bed height of 10 cm with a diameter of 7.7 mm. The column had been equilibrated prior to the anion exchange chromatography step with 3 column volumes of 20 mM Tris/1M NaCl buffer adjusted to pH 8.0 with hydrochloric acid and 5 column volumes 20 mM Tris buffer adjusted to pH 8.0 with hydrochloric acid.

The column was then washed with 5 column volumes of equilibration buffer to recover the CDP870 Fab'.

Collection of the CDP870 Fab' fraction started when the UV absorbance at 280 nm exceeded 0.5 AU/cm shortly after the start of the loading. The end of the fraction collection occurred during the wash when the UV absorbance dropped below 0.5 AU/cm. The yield for the antibody fragment on this step was 90.5%.

Example 2

CDP870 Fab' was expressed as a heterologous protein in *E. coli* host cells at a concentration of 1.9 g/L. The heterologous protein was released from the periplasmic space of the host cells by the addition of Tris-EDTA and heat treatment at 50° C. Cellular material was removed through centrifugation and the cell extract containing the heterologous protein was adjusted through addition of acetic acid to a pH 4.5. The pH adjusted cell extract was then clarified using a combination of centrifugation and depth filtration with 0.2 µm filtration.

The clarified extract (feed stream) was diluted with a dilution factor of 4 with water to achieve a conductivity of 3.5 mS/cm.

The feed stream containing the CDP870 Fab' was then loaded to about 51 g/L resin at a flow rate of 300 cm/h onto a Capto S cation exchange column from GE Healthcare [highly cross-linked rigid agarose bead (mean particle size 90 µm) with a sulphonate cation exchange ligand attached via a dextran linker (ionic capacity 0.11-0.14 mmol $Na^+$/ml)]. The Capto S cation exchange column had a column bed height of 20 cm with a diameter of 16 mm. The column had been equilibrated prior to feed stream loading with 3 column volumes of 50 mM sodium acetate/1 M NaCl buffer adjusted to pH 4.5 with acetic acid and subsequently 4 column volumes of 50 mM sodium acetate buffer adjusted to pH 4.5 with acetic acid.

After loading the column was washed with 6 column volumes of the 50 mM sodium acetate buffer adjusted to pH 4.5 with acetic acid, until the all the unbound material is washed off. The CDP870 Fab' fraction was eluted with up to 8 column volumes of buffer with 50 mM sodium acetate and 200 mM NaCl adjusted to pH 4.5 with acetic acid. The eluted CDP870 Fab' was collected when the UV absorbance at 280 nm exceeded 0.5 AU/cm until it dropped below 0.5 AU/cm.

The CDP870 Fab' pool was subjected to ultrafiltration in a centrifugal concentrator (Amicon) using a polyether sulphone-based ultrafiltration membrane with a nominal molecular weight cut-off of 10 kD resulting in a concentration of the CDP870 Fab' pool to 18 mg/mL. Subsequently diafiltration was performed until the CDP870 Fab' pool in 20 mM Tris had reached pH 8.3 and a conductivity of 1.0 mS/cm. 6 volumes of buffer were required for the diafiltration.

The CDP870 Fab' pool was loaded onto a Capto Q anion exchange chromatography column from GE Healthcare [highly cross-linked rigid agarose bead (mean particle size 90 µm) with a quaternary amine anion exchange ligand attached via a dextran linker (ionic capacity 0.16-0.22 mmol $Cl^-$/ml)] at a flow rate of 250 cm/h and applying about 30 g of CDP870 Fab' per liter of resin. The Capto™ anion exchange column had a column bed height of 10 cm with a diameter of 7.7 mm. The column had been equilibrated prior to the anion exchange chromatography step with 3 column volumes of 20 mM Tris/1M NaCl buffer adjusted to pH 8.3 with hydrochloric acid and 5 column volumes 20 mM Tris buffer adjusted to pH 8.3 with hydrochloric acid.

The column was then washed with 5 column volumes of equilibration buffer to recover the CDP870 Fab'.

Collection of the CDP870 Fab' fraction started when the UV absorbance at 280 nm exceeded 0.5 AU/cm shortly after the start of the loading. The end of the fraction collection occurred during the wash when the UV absorbance dropped below 2.0 AU/cm.

Example 3

CDP870 Fab' was expressed as a heterologous protein in *E. coli* host cells at a concentration of 2.5 g/L. The heterologous protein was released from the periplasmic space of the host cells by the addition of Tris-EDTA and heat treatment at 50° C. Cellular material was removed through centrifugation and the cell extract containing the heterologous protein was adjusted through addition of acetic acid to a pH 4.5. The pH adjusted cell extract was then clarified using a combination of centrifugation and depth filtration with 0.2 µm filtration.

The clarified extract (feed stream) was diluted with a dilution factor of 4 with water to achieve a conductivity of 4.0 mS/cm.

The feed stream containing the CDP870 Fab' was then loaded to about 60 g/L resin at a flow rate of 400 cm/h onto a Capto S cation exchange column from GE Healthcare [highly cross-linked rigid agarose bead (mean particle size 90 µm) with a sulphonate cation exchange ligand attached via a dextran linker (ionic capacity 0.11-0.14 mmol $Na^+$/ml)]. The Capto S cation exchange column had a column bed height of 24 cm with a diameter of 20 cm. The column had been equilibrated prior to feed stream loading with 3 column volumes of 50 mM sodium acetate/1 M NaCl buffer adjusted to pH 4.5 with acetic acid and subsequently 4 column volumes of 50 mM sodium acetate buffer adjusted to pH 4.5 with acetic acid.

After loading the column was washed with 6 column volumes of the 50 mM sodium acetate buffer adjusted to pH 4.5 with acetic acid, until the all the unbound material is washed off. The CDP870 Fab' fraction was eluted with up to 5 column volumes of buffer with 50 mM sodium acetate and 250 mM NaCl adjusted to pH 4.5 with acetic acid. The eluted CDP870 Fab' was collected when the UV absorbance at 280 nm exceeded 1.75 AU/cm until it dropped below 0.55 AU/cm.

The CDP870 Fab' was subjected to ultrafiltration in tangential flow mode using 0.4 $m^2$ polyethersulphone membrane with a 10 kDa nominal molecular weight cut-off (Pall 10k Omega Centramate T-Series). The CDP870 Fab' was concentrated to 51 mg/mL before diafiltration with 5.8 volumes of 20 mM Tris pH 8.5 until the pH of the Fab' solution was pH 8.5 and the conductivity was 0.8 mS/cm. The Fab' was recovered from the ultrafiltration equipment and pooled with 600 mL of 20 mM Tris pH 8.5 buffer used to wash any remaining Fab' from the system.

The CDP870 Fab' pool was loaded onto a Capto Q anion exchange chromatography column from GE Healthcare [highly cross-linked rigid agarose bead (mean particle size 90 µm) with a quaternary amine anion exchange ligand attached via a dextran linker (ionic capacity 0.16-0.22 mmol $Cl^-$/ml)] at a flow rate of 200 cm/h and applying about 37 g of CDP870 Fab' per liter of resin. The Capto Q™ anion exchange column had a column bed height of 24 cm with a diameter of 20 cm. The column had been equilibrated prior to the anion exchange chromatography step with 3 column volumes of 20 mM Tris/1M NaCl buffer adjusted to pH 8.5 with hydrochloric acid and 5 column volumes 20 mM Tris buffer adjusted to pH 8.5 with hydrochloric acid.

The column was then washed with 5 column volumes of equilibration buffer to recover the CDP870 Fab'.

Collection of the CDP870 Fab' fraction started when the UV absorbance at 280 nm exceeded 0.5 AU/cm shortly after the start of the loading. The end of the fraction collection occurred during the wash when the UV absorbance dropped below 2.0 AU/cm.

Example 4

REFERENCE LIST

Battersby, J. E., Snedecor, B., Chen, C., Champion, K. M., Riddle, L., and Vanderlaan, M. (2001). Affinity-reversed-phase liquid chromatography assay to quantitate recombinant antibodies and antibody fragments in fermentation broth. J Chromatogr A 927, 61-76.

Do, T., Ho, F., Heidecker, B., Witte, K., Chang, L., and Lerner, L. (2008). A rapid method for determining dynamic binding capacity of resins for the purification of proteins. Protein Expr. Purif. 60, 147-150.

Durany O, C. G. d. M. C. L.-S. J. (2004). Studies on the expression of recombinant fuculose-1-phosphate aldolase in *Escherichia coli*. Process Biochem 39, 1677-1684.

GE Healthcare data file 11-0025-76 AE. Ion exchange chromatography. [11-0025-76 AE]. 2007. Ref Type: Data File Glover, D. J. and Humphreys, D. P. (2004). Antibody fragments. In Antibodies, Volume 1: Production and purification, G. Subramanian, ed. (New York: Kluwer Academic/Plenum Publishers), pp. 25-73.

Holliger, P. and Hudson, P. J. (2005). Engineered antibody fragments and the rise of single domains. Nat Biotechnol 23, 1126-1136.

Humphreys, D. P. (2003). Production of antibodies and antibody fragments in *Escherichia coli* and a comparison of their functions, uses and modification. Curr Opin Drug Discov Devel 6, 188-196.

Humphreys, D. P. and Glover, D. J. (2001). Therapeutic antibody production technologies: molecules, applications, expression and purification. Curr Opin Drug Discov Devel 4, 172-185.

Humphreys, D. P., Heywood, S. P., King, L. M., Bowering, L. C., Turner, J. P., and Lane, S. E. (2004). Engineering of *Escherichia coli* to improve the purification of periplasmic Fab' fragments: changing the pI of the chromosomally encoded PhoS/PstS protein. Protein Expr. Purif. 37, 109-118.

Jana, S. and Deb, J. K. (2005). Strategies for efficient production of heterologous proteins in *Escherichia coli*. Appl Microbiol Biotechnol 67, 289-298.

Makrides, S. C. (1996). Strategies for achieving high-level expression of genes in *Escherichia coli*. Microbiol Rev 60, 512-538.

McCue, J. T., Kemp, G., Low, D., and Quinones-Garcia, I. (2003). Evaluation of protein-A chromatography media. J Chromatogr A 989, 139-153.

Spitali, M. (2009). Downstream Processing of Monoclonal Antibody Fragments. In Process scale purification of antibodies, U. Gottschalk, ed. John Wiley & Sons, Inc.), pp. 349-372.

Swartz, J. R. (2001). Advances in *Escherichia coli* production of therapeutic proteins. Curr Opin Biotechnol 12, 195-201.

Terpe, K. (2006). Overview of bacterial expression systems for heterologous protein production: from molecular and biochemical fundamentals to commercial systems. Appl Microbiol Biotechnol 72, 211-222.

Tugcu, N. (2008). Purification of proteins using displacement chromatography. Methods Mol Biol 421, 71-89.

Walsh, G. (2007). Biopharmaceuticals: Approval Trends in 2006. BioPharm International 21.

The invention claimed is:

1. A process for the purification of an antibody fragment from periplasmic cell extract comprising:
   a) a first chromatography step to capture the antibody fragment by subjecting a mixture comprising the antibody fragment and bacterial host cell protein, wherein bacterial host cell protein is present at 200 μg/ml-10,000 μg/ml and wherein the antibody fragment is at a concentration of at least 1.5 g/L in said mixture, to cation exchange chromatography and subsequent elution, thereby producing a first eluate containing the antibody fragment; and
   b) a second chromatography step wherein the first eluate is subjected to anion exchange chromatography to capture impurities and produce a flow through containing the antibody fragment.

2. The process according to claim 1, wherein the process comprises not more than two chromatography steps.

3. The process according to claim 1, wherein all chromatography steps are performed on a chromatography column.

4. The process according to claim 1, wherein the cation exchange chromatography is performed in elution mode.

5. The process according to claim 1, wherein the first cation chromatography step comprises the following steps in sequential order:
   a) loading a mixture containing an antibody fragment onto the cation exchange column,
   b) washing the cation exchange column with a wash buffer wherein during the washing the conductivity, pH and salt concentration of the buffer remains essentially unchanged, and
   c) eluting the antibody fragment with an elution buffer.

6. The process according to claim 5, wherein the pH of the washing buffer is identical to the pH of the mixture containing an antibody fragment prior to first chromatography step.

7. The process according to claim 5, wherein the mixture containing an antibody fragment, prior to the first chromatography step has a pH of between 4.0 to 5.0.

8. The process according to claim 5, wherein the antibody fragment is eluted with a buffer that has a higher pH, a higher conductivity or both a higher pH and higher conductivity than the wash buffer.

9. The process according to claim 1, wherein the cation exchange chromatography in the first chromatography step is performed at a flow rate of at least 300 cm/h.

10. The process according to claim 1, wherein the cation exchange chromatography in the first chromatography step is performed at a conductivity of not more 6 mS/cm.

11. The process according to claim 1, wherein the cation exchange chromatography in the first chromatography step is performed in a chromatography column comprising sulphonyl, sulphopropyl or carboxymethyl coupled to a resin.

12. The process according to claim 1, wherein the cation exchange chromatography column in the first chromatography step has a dynamic binding capacity for the antibody fragment of between 50 and 75 g/L resin.

13. The process according to claim 11, wherein the cation exchange chromatography column resin in the first chromatography step has a mean particular size of at least 50 μm.

14. The process according to claim 1, wherein in the cation exchange chromatography of the primary capture step between 5 and 100 g antibody fragment per liter resin are loaded.

15. The process according to claim 1, wherein the anion exchange chromatography in the second chromatography step is performed on a resin comprising quaternary ammonium (Q), diethylaminoethyl (DEAF) or trimethylaminoethyl (TMAE).

16. The process according to claim 1, wherein the antibody fragment is a Fab, Fab' or scFv.

17. The process according to claim 16, wherein the Fab or Fab' binds specifically to VEGF-A, FeRn, OX40, glycoprotein IIb/IIIa receptor, C5, HER2/neu, TNFα, IL1β or CD40-L.

18. The process according to claim 17, wherein the Fab or Fab' is abciximab, ranibizumab, pexelizumab, CDP870 or CDP7657.

19. The process according to claim 1, wherein the antibody fragment recovered from the process contains host cell protein in an amount of not more than 150 parts per million.

20. The process according to claim 1, said process further comprising ultrafiltration of the first eluate and ultrafiltration of the flow through containing the antibody fragment.

* * * * *

SEQUENCE LISTING

<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: CDP870 CDR-H1

<400> SEQUENCE: 1

Asp Tyr Gly Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: CDP870 CDR-H2

<400> SEQUENCE: 2

Trp Ile Asn Thr Tyr Ile Gly Glu Pro Ile Tyr Ala Asp Ser Val Lys
1               5                   10                  15

Gly

<210> SEQ ID NO 3
<211> LENGTH: 9
<212> TYPE: PRT
<213> ORGANISM: Artificial Sequence
<220> FEATURE:
<223> OTHER INFORMATION: CDP870 CDR-H3

<400> SEQUENCE: 3

Gly Tyr Arg Ser Tyr Ala Met Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: CDP870 CDR-L1

<400> SEQUENCE: 4

Lys Ala Ser Gln Asn Val Gly Thr Asn Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDP870 CDR-L2

<400> SEQUENCE: 5

Ser Ala Ser Phe Leu Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDP870 CDR-L3

<400> SEQUENCE: 6

Gln Gln Tyr Asn Ile Tyr Pro Leu Thr
1               5

<210> SEQ ID NO 7
<211> LENGTH: 107
<212> TYPE: PRT
<213> ORGANISM: Artificial Sequence
<220> FEATURE:
<223> OTHER INFORMATION: CDP870 variable light chain

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105

<210> SEQ ID NO 8
<211> LENGTH: 118
<212> TYPE: PRT
<213> ORGANISM: Artificial Sequence
<220> FEATURE:
<223> OTHER INFORMATION: CDP870 variable heavy chain

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115

<210> SEQ ID NO 9
<211> LENGTH: 214
<212> TYPE: PRT
<213> ORGANISM: Artificial Sequence
<220> FEATURE:
<223> OTHER INFORMATION: CDP870 light chain

```
<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 229
<212> TYPE: PRT
<213> ORGANISM: Artificial Sequence
<220> FEATURE:
<223> OTHER INFORMATION: CDP870 heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125
```

-continued

```
Leu Ala Pro Ser Ser Lys Ser Thr Ser Gly Gly Thr Ala Ala Leu Gly
    130             135             140

Cys Leu Val Lys Asp Tyr Phe Pro Glu Pro Val Thr Val Ser Trp Asn
145             150             155             160

Ser Gly Ala Leu Thr Ser Gly Val His Thr Phe Pro Ala Val Leu Gln
            165             170             175

Ser Ser Gly Leu Tyr Ser Leu Ser Ser Val Val Thr Val Pro Ser Ser
            180             185             190

Ser Leu Gly Thr Gln Thr Tyr Ile Cys Asn Val Asn His Lys Pro Ser
        195             200             205

Asn Thr Lys Val Asp Lys Lys Val Glu Pro Lys Ser Cys Asp Lys Thr
    210             215             220

His Thr Cys Ala Ala
225
```